United States Patent
Kasai et al.

(10) Patent No.: US 11,238,590 B2
(45) Date of Patent: Feb. 1, 2022

(54) DYNAMIC IMAGE PROCESSING APPARATUS

(71) Applicant: Konica Minolta, Inc., Tokyo (JP)

(72) Inventors: Satoshi Kasai, Hachioji (JP); Akinori Tsunomori, Kodaira (JP)

(73) Assignee: KONICA MINOLTA, INC., Tokyo (JP)

( * ) Notice: Subject to any disclaimer, the term of this patent is extended or adjusted under 35 U.S.C. 154(b) by 43 days.

(21) Appl. No.: 16/922,557

(22) Filed: Jul. 7, 2020

(65) Prior Publication Data

US 2020/0334816 A1 Oct. 22, 2020

Related U.S. Application Data

(63) Continuation of application No. 15/863,108, filed on Jan. 5, 2018, now Pat. No. 10,748,286.

(30) Foreign Application Priority Data

Jan. 10, 2017 (JP) .............................. JP2017-001537

(51) Int. Cl.
*G06T 7/00* (2017.01)
*G06K 9/00* (2006.01)
(Continued)

(52) U.S. Cl.
CPC ............ *G06T 7/0014* (2013.01); *A61B 6/469* (2013.01); *A61B 6/486* (2013.01); *A61B 6/503* (2013.01);
(Continued)

(58) Field of Classification Search
CPC ......... G06T 7/0014; G06T 7/174; G06T 7/11; G06T 7/74; G06T 7/0016; G06T 7/00;
(Continued)

(56) References Cited

U.S. PATENT DOCUMENTS

2003/0190010 A1 10/2003 Tsujii
2003/0227467 A1 12/2003 Hara
(Continued)

FOREIGN PATENT DOCUMENTS

JP    2007268154 A    10/2007
JP    2012110399 A     6/2012
(Continued)

OTHER PUBLICATIONS

JPO, Office Action for the corresponding Japanese patent application No. 2017-001537, dated Dec. 15, 2020, with English translation.
(Continued)

*Primary Examiner* — Jose L Couso
(74) *Attorney, Agent, or Firm* — Lucas & Mercanti, LLP

(57) ABSTRACT

A dynamic image processing apparatus includes a hardware processor. The hardware processor extracts (i) a region of interest and/or (ii) a frame image of interest from a series of frame images obtained by dynamic imaging of a subject. Further, the hardware processor stores, of the series of the frame images, only (i) the extracted region of interest, (ii) the extracted frame image of interest or (iii) the extracted region of interest in the extracted frame image of interest in a storage.

11 Claims, 4 Drawing Sheets

(51) Int. Cl.
| | | |
|---|---|---|
| *G06K 9/46* | (2006.01) | |
| *G06T 7/73* | (2017.01) | |
| *A61B 6/00* | (2006.01) | |
| *G06K 9/34* | (2006.01) | |
| *G06K 9/32* | (2006.01) | |
| *G06T 7/174* | (2017.01) | |
| *G06T 7/11* | (2017.01) | |
| *A61B 6/12* | (2006.01) | |

(52) U.S. Cl.
CPC .......... *A61B 6/5217* (2013.01); *A61B 6/5264* (2013.01); *A61B 6/5288* (2013.01); *G06K 9/00973* (2013.01); *G06K 9/3233* (2013.01); *G06K 9/346* (2013.01); *G06K 9/46* (2013.01); *G06T 7/11* (2017.01); *G06T 7/174* (2017.01); *G06T 7/74* (2017.01); *A61B 6/12* (2013.01); *G06K 2209/05* (2013.01); *G06T 2207/10116* (2013.01); *G06T 2207/20132* (2013.01); *G06T 2207/30048* (2013.01); *G06T 2207/30061* (2013.01)

(58) Field of Classification Search
CPC ..................... G06T 7/20; G06T 7/0012; G06T 2207/20132; G06T 2207/10116; G06T 2207/30016; G06T 2207/30048; G06T 2207/10016; G06T 2207/10024; G06T 2207/20021; G06T 2207/10072; G06T 2207/10076; G06T 2207/10081; G06T 2207/10101; G06T 2207/10104; G06T 2207/10108; G06T 2207/10112; G06T 2207/10121; G06T 2207/30068; G06T 2207/30004; G06T 2210/41; A61B 6/469; A61B 6/5288; A61B 6/486; A61B 6/5264; A61B 6/5217; A61B 6/503; A61B 6/12; A61B 6/4291; A61B 6/4405; A61B 6/463; A61B 6/468; A61B 6/507; A61B 6/5205; A61B 6/5235; A61B 6/5258; A61B 6/542; A61B 6/48; A61B 6/461; A61B 6/541; G06K 9/346; G06K 9/3233; G06K 9/00973; G06K 9/46; G06K 9/00496; G06K 9/6212; G06K 9/6229; G06K 9/00751; G06K 9/3241; G06K 9/00765; G06K 2209/05; G16H 40/20; G16H 50/20; G16H 50/30; G16H 30/40; Y10S 378/901; G06F 19/321; G06F 19/3481

See application file for complete search history.

(56) References Cited

U.S. PATENT DOCUMENTS

| | | | |
|---|---|---|---|
| 2004/0151358 A1* | 8/2004 | Yanagita | G16H 30/40 382/132 |
| 2005/0025365 A1 | 2/2005 | Oosawa | |
| 2005/0054916 A1 | 3/2005 | Mostafavi | |
| 2005/0135665 A1* | 6/2005 | Shinbata | G06T 5/40 382/132 |
| 2005/0285812 A1 | 12/2005 | Shimayama et al. | |
| 2006/0074306 A1* | 4/2006 | Greathouse | G01T 1/1647 600/431 |
| 2008/0107229 A1 | 5/2008 | Thomas et al. | |
| 2009/0097731 A1* | 4/2009 | Sanada | A61B 5/418 382/132 |
| 2009/0123051 A1 | 5/2009 | Tamai et al. | |
| 2011/0170658 A1 | 7/2011 | Arakita et al. | |
| 2012/0020452 A1 | 1/2012 | Arakita et al. | |
| 2012/0093278 A1 | 4/2012 | Tsukagoshi et al. | |
| 2012/0245453 A1 | 9/2012 | Tryggestad et al. | |
| 2013/0140712 A1 | 6/2013 | Chen | |
| 2017/0014093 A1* | 1/2017 | Hosoki | A61B 6/54 |
| 2017/0065832 A1 | 3/2017 | Berlinger et al. | |
| 2017/0071672 A1 | 3/2017 | Shochat | |
| 2017/0143289 A1* | 5/2017 | Fouras | A61B 5/7282 |
| 2019/0050664 A1 | 2/2019 | Yang et al. | |

FOREIGN PATENT DOCUMENTS

| | | |
|---|---|---|
| JP | 2012-239796 A | 12/2012 |
| JP | 2013-027696 A | 2/2013 |
| JP | 2013-075065 A | 4/2013 |
| JP | 2013172782 A | 9/2013 |
| JP | 2014-079312 A | 5/2014 |
| JP | 2016-087325 A | 5/2016 |

OTHER PUBLICATIONS

Office Action for the corresponding Japanese patent application No. 2017-001537 dated Aug. 25, 2020 and English translation.

JPO, Office Action for the corresponding Japanese patent application No. 2017-001537, dated Jun. 2, 2020, with English translation.

* cited by examiner

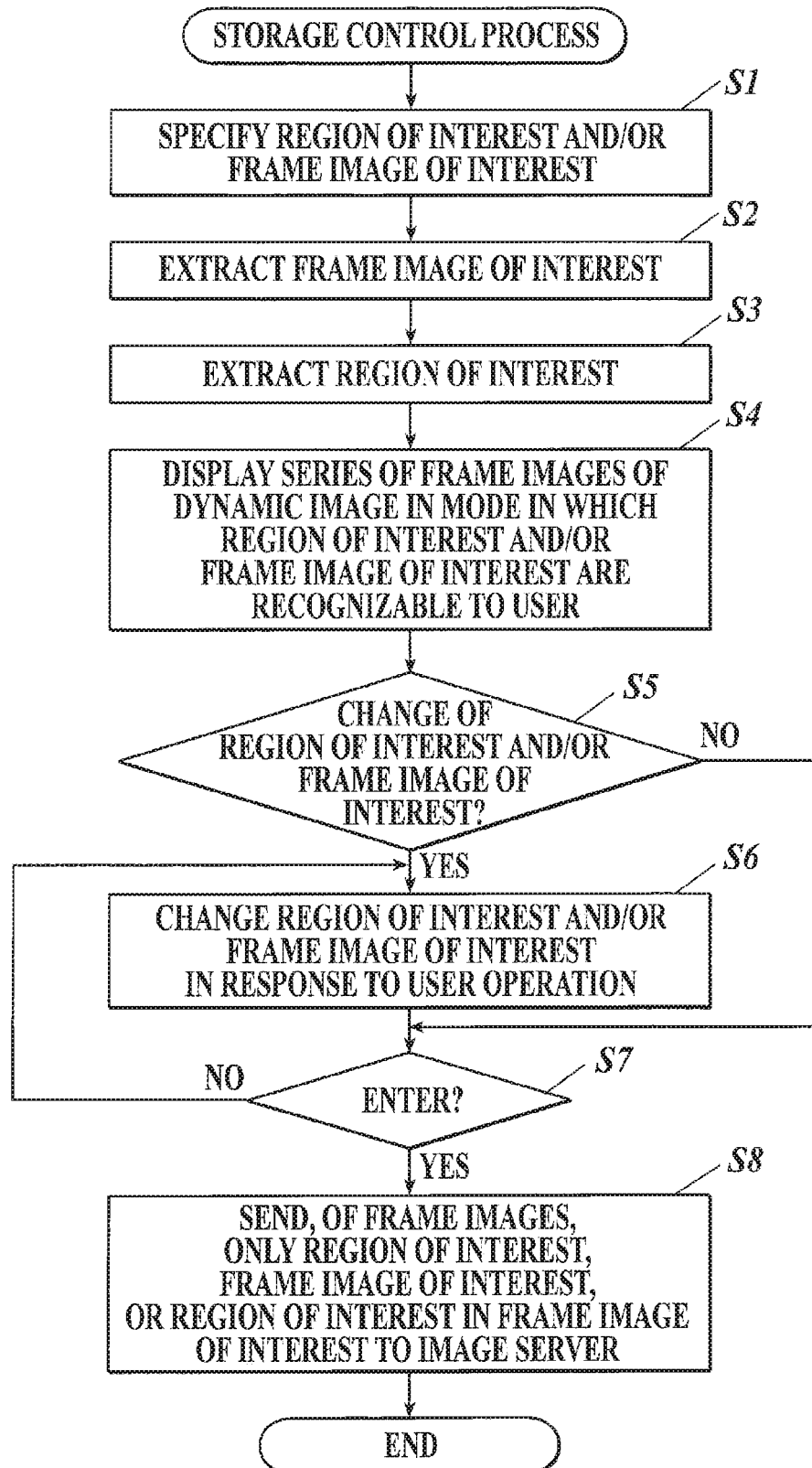

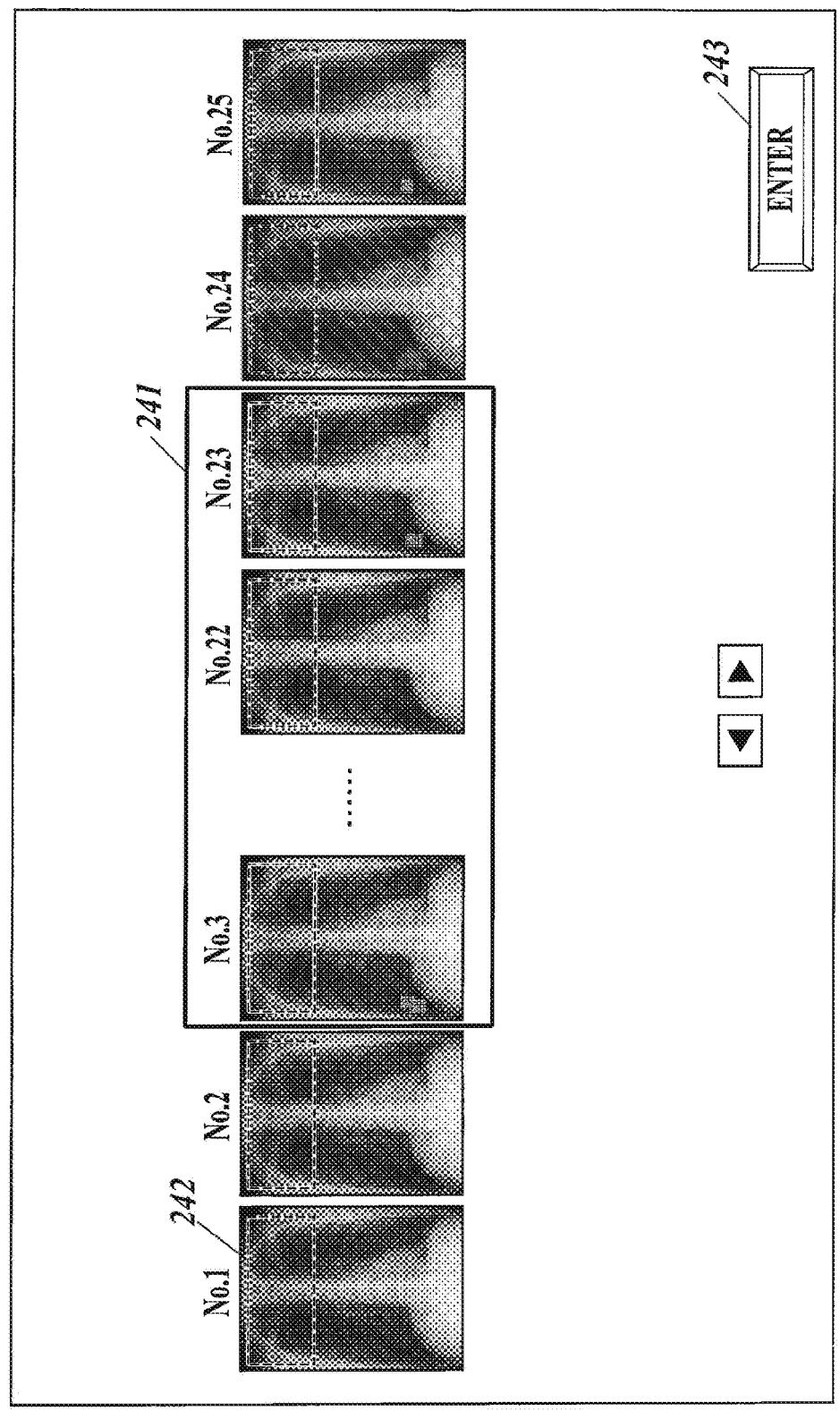

DYNAMIC IMAGE PROCESSING APPARATUS

CROSS REFERENCE TO RELATED APPLICATION

This application is a continuation of U.S. patent application Ser. No. 15/863,108 filed Jan. 5, 2018, which in term claimed priority of Japanese Patent Application No. 2017-001537, filed on Jan. 10, 2017, the contents of both applications are incorporated herein by reference.

BACKGROUND

1. Technological Field

The present invention relates to a dynamic image processing apparatus.

2. Description of the Related Art

There have been attempts to utilize, for diagnosis, a dynamic image of a subject taken with a semiconductor image sensor, such as an FPD (Flat Panel Detector), instead of or in addition to a radiation (X-ray) still image of a subject taken with a film/screen or a photostimulable phosphor plate. More specifically, by making use of high responsivity of a semiconductor image sensor in reading/deleting image data, a dynamic state of a subject is imaged (photographed) by continuously emitting pulsed radiation from a radiation source in sync with timing of image reading/deletion by the semiconductor image sensor and performing imaging multiple times per second. A series of images obtained by the imaging are displayed in order, so that doctors can recognize a series of movements of the subject.

Further, it has been proposed to analyze a series of frame images obtained by dynamic imaging, thereby generating diagnostic support information, and provide the diagnostic support information to doctors for early diagnosis.

For example, there are described in Japanese Patent Application Publication No. 2012-239796 generating diagnostic support information on breathing and diagnostic support information on perfusion on the basis of a dynamic chest image obtained by one dynamic imaging, and displaying the generated information.

By the way, a dynamic image is composed of a plurality of frame images. Hence, a necessary storage capacity per dynamic imaging (i.e. a necessary storage capacity to store a dynamic image) is larger than that to store a still image. For example, for dynamic chest images, the necessary storage capacity per dynamic imaging is about 1.5 GB. If analysis is performed about both ventilation and perfusion on the basis of a dynamic image as described in Japanese Patent Application Publication No. 2012-239796 and the analysis results are generated as moving images, the necessary storage capacity is three times as large as the above.

In general, a dynamic image(s) is compressed with a prescribed format (e.g. MPEG) and stored, but the compression amount is not enough. Further, each time a doctor performs re-interpretation of the dynamic image, he/she needs to retrieve and see all the frame images of the dynamic image and spends much time accordingly.

SUMMARY

Objects of the present invention include reducing the storage capacity necessary to store a dynamic image and letting a doctor see the portion of a dynamic image to be noted efficiently.

To achieve at least one of the abovementioned objects, according to an aspect of the present invention, there is provided a dynamic image processing apparatus including a hardware processor that: extracts (i) a region of interest and/or (ii) a frame image of interest from a series of frame images obtained by dynamic imaging of a subject; and stores, of the series of the frame images, only (i) the extracted region of interest, (ii) the extracted frame image of interest or (iii) the extracted region of interest in the extracted frame image of interest in a storage.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention, wherein:

FIG. 3 is a flowchart of a storage control process that is performed by a controller shown in FIG. 2;

FIG. 5 shows an example of a screen that is displayed on a display in Step S4 in FIG. 3.

DETAILED DESCRIPTION OF EMBODIMENTS

Hereinafter, one or more embodiments of the present invention will be described with reference to the drawings. However, the scope of the invention is not limited to the disclosed embodiments.

[Configuration of Dynamic Image Processing System 100]

First, configuration of this embodiment is described.

Figure 1:
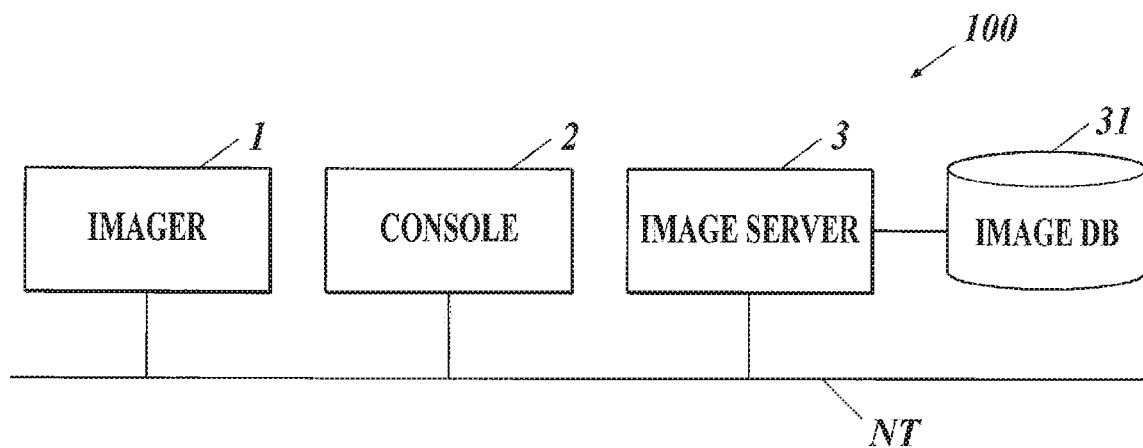
FIG. 1 shows overall configuration of a dynamic image processing system according to one or more embodiments of the present invention.

FIG. 1 shows overall configuration of a dynamic image processing system 100 according to this embodiment of the present invention.

As shown in FIG. 1, the dynamic image processing system 100 includes an imager 1, a console 2 and an image server 3 connected one another via a communication network NT, such as a LAN (Local Area Network). These apparatuses of the dynamic image processing system 100 are in conformity with DICOM (Digital Image and Communications in Medicine) standard and communicate with one another in conformity with DICOM.

The imager 1 includes a radiation source and an FPD. The imager 1 repeatedly emits pulsed radiation, such as pulsed X-rays, to a subject placed between the radiation source and the FPD at predetermined time intervals (pulse emission) or continuously emits radiation without a break to the subject at a low dose rate (continuous emission), thereby obtaining a plurality of images showing the dynamic state of the subject (i.e. performing dynamic imaging (kinetic imaging) of the subject), and sends the obtained images to the console 2. A series of images obtained by dynamic imaging is called a dynamic image Images constituting a dynamic image are called frame images. In this embodiment, the imager 1 performs dynamic imaging of a chest, thereby obtaining a plurality of frame images showing change in shape of the lungs by expansion and contraction of the lungs with breathing, pulsation of the heart, and so forth, attaches supplementary information, such as patient information and examination information (imaging site, imaging date and time, etc.), to the obtained series of frame images, and sends the same to the console 2.

The console 2 is a dynamic image processing apparatus that analyzes the dynamic image sent from the imager 1, thereby extracting a region of interest and/or a frame image(s) of interest to be noted in diagnosis, and sends the same to the image server 3.

Figure 2:
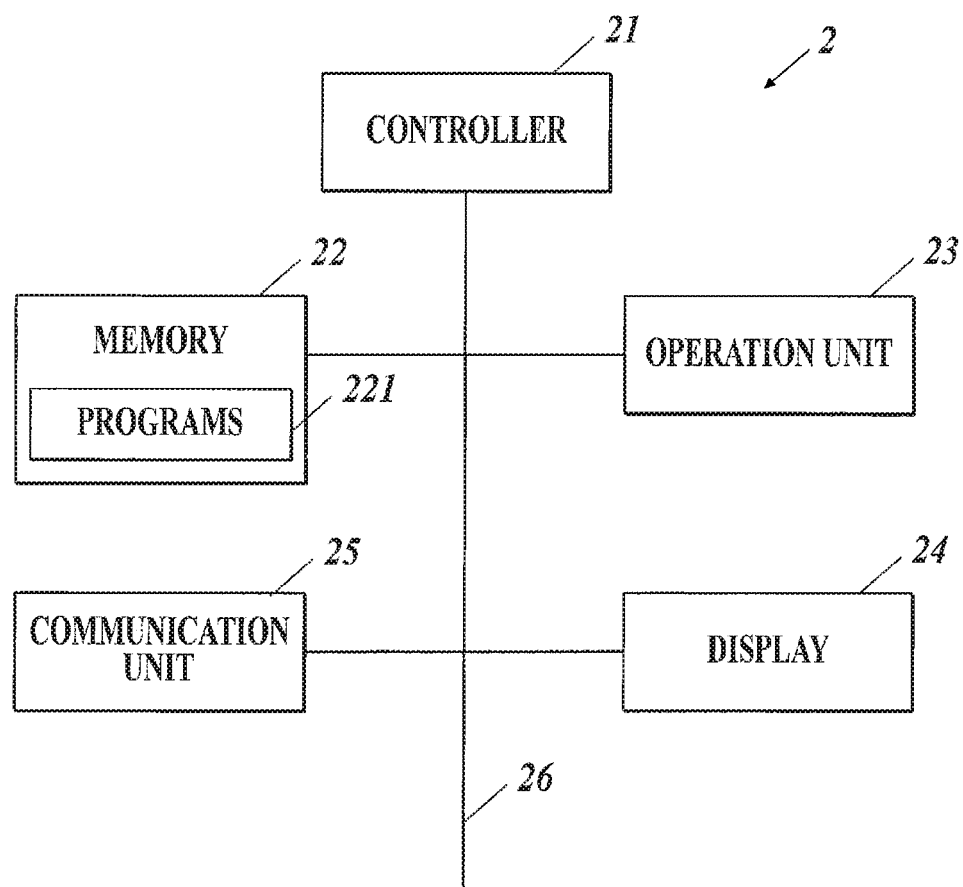
FIG. 2 is a block diagram showing functional configuration of a console shown in FIG. 1.

FIG. 2 shows an example of functional configuration of the console 2. As shown in FIG. 2, the console 2 includes a controller 21, a memory 22, an operation unit 23, a display 24 and a communication unit 25. These units or the like are connected to one another via a bus 26.

The controller 21 includes a CPU (Central Processing Unit; hardware processor) and a RAM (Random Access Memory). The CPU of the controller 21 reads out programs 221 stored in the memory 22 in response to operations on the operation unit 23, opens the read-out programs 221 in the RAM, and performs various processes, such as the below-described storage control process, in accordance with the opened programs 221.

The memory 22 is constituted of a nonvolatile semiconductor memory, a hard disk or the like. The memory 22 stores therein the programs 221 to be executed by the controller 21, parameters necessary to perform the processes of the programs 221, data, such as process results, and so forth.

The operation unit 23 includes: a keyboard including cursor keys, number input keys and various function keys; and a pointing device, such as a mouse, and outputs, to the controller 21, command signals input by a user operating the keys on the keyboard or the mouse. The operation unit 23 may have a touchscreen on the display screen of the display 24. In this case, the operation unit 23 outputs command signals input via the touchscreen to the controller 21.

The display 24 is constituted of a monitor, such as an LCD (Liquid Crystal Display) or a CRT (Cathode Ray Tube), and displays thereon input commands from the operation unit 23, data and so forth in accordance with commands of display signals input from the controller 21.

The communication unit 25 includes a LAN adapter, a modem and a TA (Terminal Adapter), and controls data exchange with apparatuses connected to the communication network NT.

The image server 3 is a computer apparatus that includes a controller, a memory, an operation unit, a display and a communication unit. The memory of the image server 3 is provided with an image DB (DataBase) 31. The image DB 31 stores therein dynamic images sent from the console 2 associated with the supplementary information, such as patient information and examination information.

[Actions of Dynamic Image Processing System 100]

Next, actions of the dynamic image processing system 100 according to this embodiment are described.

First, the imager 1 performs dynamic imaging of the chest of a patient as the subject, and sends a series of frame images of a dynamic image obtained thereby to the console 2.

When receiving the dynamic image from the imager 1 through the communication unit 25, the console 2 performs a storage control process.

FIG. 3 shows the storage control process that is performed by the controller 21 of the console 2. The storage control process is performed by the controller 21 in corporation with the program(s) 221 stored in the memory 22.

First, the controller 21 causes the display 24 to display a screen to specify the region of interest and the frame image (one or more frame images) of interest, and accepts the region of interest and/or the frame image of interest specified through the operation unit 23 (Step S1).

Any of both lung fields, the right lung field, the left lung field, the upper part of the lung fields, the middle part of the lung fields, the lower part of the lung fields, an abnormal region(s), a lung field containing an abnormal region(s) and so forth can be specified as the region of interest. In addition, any of frame images for one respiratory cycle, frame images for one heartbeat, a frame image(s) containing an abnormal region(s) and so forth can be specified as the frame image of interest. In Step S1, either the region of interest or the frame image of interest may be specified, or both the region of interest and the frame image of interest may be specified.

Next, the controller 21 extracts the frame image of interest from the series of the frame images of the dynamic image (hereinafter may be referred to as the "frame images of the dynamic image) (Step S2).

Note that one respiratory cycle is composed of the expiratory phase and the inspiratory phase. In the expiratory phase, the diaphragm rises, so that the air is released from the lungs (lung fields), and accordingly the lung fields become small. This increases density of the lung fields, and in a dynamic image, the lung fields are depicted in low density values (signal values). At the maximal expiratory level, the position of the diaphragm is the highest (the distance between the diaphragm and an apex of lung is the shortest). In the inspiratory phase, the diaphragm lowers, so that the air is taken into the lungs (lung fields), and accordingly the lung fields become large. This decreases density of the lung fields, and in a dynamic image, the lung fields are depicted in high density values. At the maximal inspiratory level, the position of the diaphragm is the lowest (the distance between the diaphragm and the apex of lung is the longest).

Hence, when frame images for one respiratory cycle are specified as the frame image of interest, the controller 21 identifies at least one of a frame image at the maximal expiratory level and a frame image at the maximal inspiratory level, and extracts frame images for one respiratory cycle on the basis of the identified frame image or frame images. For example, the controller 21 extracts a frame image at the maximal expiratory level (or maximal inspiratory level) to the frame image at the following maximal expiratory level (or maximal inspiratory level) as frame images for one respiratory cycle.

For example, the controller 21 recognizes the position of the diaphragm in each frame image of the dynamic image, and identifies a frame image at the maximal expiratory level and a frame image at the maximal inspiratory level on the basis of the position of the diaphragm recognized in each frame image of the dynamic image. More specifically, the controller 21 first, in each frame image of the dynamic image, recognizes the region(s) of a lung field(s) (lung field regions) and obtains a point having an x coordinate on the contour of the bottom of the lung field region as a reference point of the diaphragm, and identifies a frame image having a local minimum distance between the reference point of the diaphragm and the apex of lung in y direction, which is the vertical direction, as a frame image at the maximal expiratory level and a frame image having a local maximum distance therebetween as a frame image at the maximal inspiratory level. The horizontal direction and the vertical direction of each frame image are x direction and y direction, respectively.

Alternatively, the controller 21 may, in each frame image of the dynamic image, recognize a lung field region(s) and calculate the area of the recognized lung field region, and identify a frame image having a local minimum area of the lung field region as a frame image at the maximal expiratory level and a frame image having a local maximum area of the lung field region as a frame image at the maximal inspiratory level. The area of the lung field region is obtained, for example, by counting the number of pixels of the lung field region and multiplying the number of pixels of the lung field region by the size of a pixel. This method is effective for a dynamic image(s) taken in the state in which the diaphragm hardly moves because of, for example, disease or imaging in the decubitus position.

Still alternatively, the controller 21 may recognize a lung field region(s) in each frame image of the dynamic image, and identify a frame image at the maximal expiratory level and a frame image at the maximal inspiratory level on the basis of the movement of the outer lateral of the lung field region (expansion in the horizontal direction). More specifically, the controller 21 first obtains a point having a y coordinate on the contour of the outer lateral of the lung field region as a reference point in each frame image of the dynamic image, and identifies a frame image in which the reference point has a local minimum x coordinate in the outside direction of the lung field region as a frame image at the maximal expiratory level and a frame image in which the reference point has a local maximum x coordinate in the outside direction thereof as a frame image at the maximal inspiratory level. This method is effective for a dynamic image(s) of a patient(s) whose breathing style is mainly chest breathing.

Any method can be used for recognition of the lung field region(s). For example, a threshold value is obtained from a histogram of signal values (density values) of pixels of a frame image by discriminant analysis, and a region having a higher signal value(s) than the threshold value is extracted as a lung field region candidate. Then, edge detection is performed on around the border of the extracted lung field region candidate, and, in small regions around the border, points where the edge is the maximum are extracted along the border. Thus, the border of the lung field region can be extracted.

When frame images for one heartbeat are specified as the frame image of interest, the controller 21 first recognizes the region of the heart (heart region) in each frame image of the dynamic image. Any known method can be used for recognition of the heart region. For example, a template image of heart is stored in the memory 22 in advance, and the controller 21 recognizes the heart region in each frame image of the dynamic image by temperate matching. Next, the controller 21 identifies frame images for one heartbeat on the basis of change in density of the recognized heart region, and extracts the identified frame images as the frame image of interest. For example, the controller 21 sets an ROI in a region where the heart regions of the respective frame images overlap, and extracts the frame image at a local minimum (or local maximum) of the waveform (density waveform) of a representative value (e.g. the mean, the median, the maximum, etc.) of signal values (density values) of the ROI to the frame image at the next local minimum (or local maximum) as frame images for one heartbeat.

Preferably, time-direction high-pass filtering (e.g. a cutoff frequency of 0.85 Hz) is performed on the density waveform of the ROI set in the region where the heart regions of the respective frame images overlap. This can remove the low-frequency component due to noise or the like from the density waveform and can obtain the signal component due to perfusion (blood flow). Alternatively, bandpass filtering (e.g. a lower cutoff frequency of 0.8 Hz and an upper cutoff frequency of 2.4 Hz) may be performed on the density waveform to remove the low-frequency component.

When a frame image(s) containing an abnormal region(s) is specified as the frame image of interest, the controller 21 performs an abnormal shadow region candidate detection process on each frame image of the dynamic image, and extracts a frame image(s) in which an abnormal shadow region candidate(s) is detected as the frame image of interest.

Any known method can be used for the abnormal shadow region candidate detection process. For example, the process described in Japanese Patent Application Publication No. 2005-198890 is applicable. The process includes, for each frame image, (i) generating an emphasized image by emphasizing a region(s) where gradient vectors of pixel values of the frame image gather, (ii) binarizing the emphasized image using multiple threshold values, (iii) detecting, in each obtained binarized image, an abnormal shadow region candidate(s) among regions in each of which pixels having pixel values equal to or more than the threshold value are adjacent to one another, on the basis of at least one of the shape, the size and a statistic of pixel values of each of the regions, and (iv) detecting, on the basis of the number of times the abnormal shadow region candidate is detected at the same position in the multiple binarized images, false positive abnormal shadow region candidates. In Japanese Patent Application Publication No. 2005-198890, the lighter the color is (the lower the density is), the higher the pixel value is.

Alternatively, any of the methods described, for example, in U.S. Pat. Nos. 5,987,094 and 6,760,468 may be used.

Next, the controller 21 extracts the region of interest (Step S3).

The region of interest may be extracted from each frame image of the dynamic image or only from each frame image of interest. In this embodiment, the region of interest is extracted from each frame image of the dynamic image.

Figure 4A:
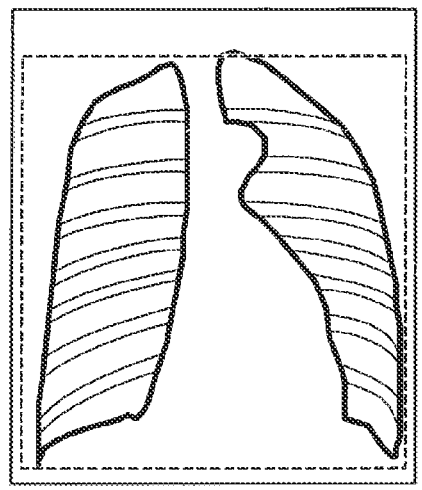
FIG. 4A shows, with a dotted line, a region extracted as a region of interest when both lung fields are specified as the region of interest.

When both lung fields are specified as the region of interest, the controller 21 recognizes the lung field regions in each frame image of the dynamic image, and extracts, as indicated by a dotted line in FIG. 4A, a rectangular region enclosing (e.g. circumscribing) the lung field regions as the region of interest from each frame image of the dynamic image.

When either the right lung field or the left lung field is specified as the region of interest, the controller 21 extracts a rectangular region enclosing (e.g. circumscribing) the specified (right or left) lung field as the region of interest from each frame image of the dynamic image.

Figure 4B:
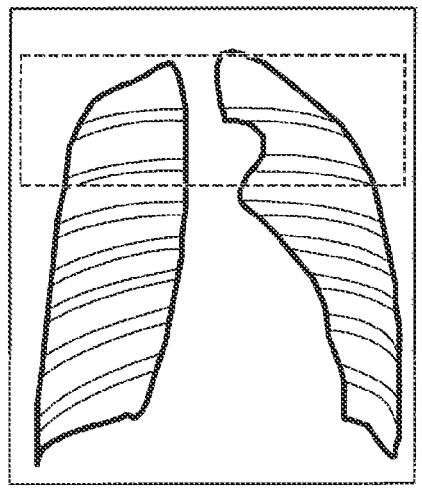
FIG. 4B shows, with a dotted line, a region extracted as the region of interest when the upper part of the lung fields is specified as the region of interest.

When the upper part of the lung fields, the middle part of the lung fields or the lower part of the lung fields is specified as the region of interest, the controller 21 recognizes the lung field regions (the region enclosing the lung fields) in each frame image of the dynamic image, horizontally divides the recognized lung field regions into three parts of the upper part, the middle part and the lower part, and extracts a rectangular region enclosing the specified part as the region of interest from each frame image of the dynamic image. FIG. 4B shows, with a dotted line, the region extracted as the region of interest when the upper part of the lung fields is specified as the region of interest.

Figure 4C:
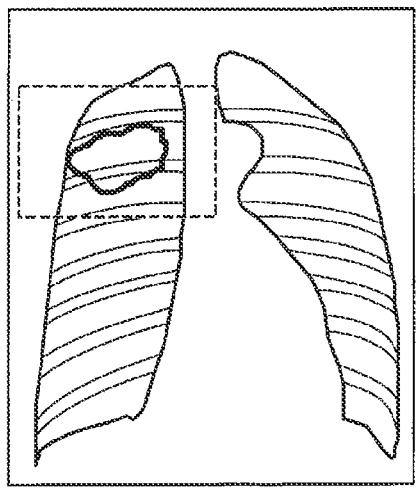
FIG. 4C shows, with a dotted line, a region extracted as the region of interest when an abnormal region is specified as the region of interest.

When an abnormal region(s) is specified as the region of interest, the controller 21 performs the abnormal shadow region candidate detection process on each frame image of the dynamic image, thereby detecting an abnormal shadow region candidate(s), and extracts, as indicated by a dotted line in FIG. 4C, a region containing the detected abnormal shadow region candidate (e.g. a rectangular region enclosing the abnormal shadow region candidate) as the region of interest. When a lung field containing an abnormal region(s) is specified as the region of interest, the controller 21 extracts a rectangular region enclosing (e.g. circumscribing) the lung field containing the detected abnormal shadow region candidate (e.g. the left lung field if an abnormal shadow region candidate(s) is found in the left lung field) as the region of interest.

Next, the controller 21 displays the series of the frame images of the dynamic image in a line on the display 24 in a mode in which the extracted region of interest and/or the extracted frame image of interest are recognizable to the user (Step S4).

FIG. 5 shows an example of the screen that is displayed on the display 24 in Step S4. As shown in FIG. 5, for example, the extracted frame image of interest is recognizably displayed with a frame 241, and also the extracted region of interest is recognizably displayed with frames 242. The frame 241 and the frames 242 can be widen, narrowed or moved in response to operations on the operation unit 23. Widening, narrowing or moving the frame 241 and the frames 242 can make commands to change the frame image of interest and the region of interest, respectively. A press on an enter button 243 on the screen can enter and fix the region of interest and the frame image of interest.

Next, the controller 21 determines whether a command(s) to change the region of interest and/or the frame image of interest is made through the operation unit 23 (Step S5).

When determining that a command(s) to change the region of interest and/or the frame image of interest is made (Step S5; YES), the controller 21 changes the region of interest and/or the frame image of interest in response to an operation(s) on the operation unit 23 (Step S6), and then proceeds to Step S7.

On the other hand, when determining that a command(s) to change the region of interest and/or the frame image of interest is not made (Step S5; NO), the controller 21 proceeds to Step S7.

In Step S7, the controller 21 determines whether the enter button 243 is pressed through the operation unit 23 (Step S7).

When determining that the enter button 243 is not pressed (Step S7; NO), the controller 21 returns to Step S6.

On the other hand, when determining that the enter button 243 is pressed (Step S7; YES), the controller 21 cuts out the region of interest, the frame image of interest or the region of interest in the frame image of interest from the frame images of the dynamic image, and sends a dynamic image formed of only the cut-out images to the image server 3 through the communication unit 25 (Step S8), and then ends the storage control process. When only the region of interest is specified in Step S1, the controller 21 cuts out the region of interest from each frame image of the dynamic image and sends the same as a dynamic image (e.g. a video file) to the image server 3. When only the frame image of interest is specified in Step S1, the controller 21 cuts out the frame image of interest from the frame images of the dynamic image and sends the same as a dynamic image to the image server 3. When both the region of interest and the frame image of interest are specified in Step S1, the controller 21 cuts out the region of interest in the frame image of interest and sends the same as a dynamic image to the image server 3.

In Step S8, preferably, the controller 21 puts information on the specified region of interest and/or frame image of interest in the supplementary information on the dynamic image, and sends the same to the image server 3. By this, when a user retrieves the dynamic image from the image server 3, he/she can readily understand which portion of the original dynamic image has been cut out to form the retrieved dynamic image.

When receiving the dynamic image from the console 2, the image server 3 stores the received dynamic image in the image DB 31. When receiving a command to read out a dynamic image from the console 2 by patient information, examination information and so forth being specified therewith, the image server 3 reads out and sends the specified dynamic image to the console 2.

Thus, the controller 21 of the console 2 generates a dynamic image formed of, of a series of frame images of a dynamic image obtained by the imager 1, only (i) images of the region of interest in the frame images of the dynamic image, (ii) the frame image of interest or (iii) images of the region of interest in the frame image of interest, sends the generated dynamic image to the image server 3 through the communication unit 25, and stores the dynamic image in the image DB 31 of the image server 3. This can reduce the storage capacity necessary to store a dynamic image. Further, of a series of frame images of a dynamic image, only the portion to be noted is stored. This can let a doctor see the portion of a dynamic image to be noted at the time of interpretation of the dynamic image efficiently.

The controller 21 may analyze the dynamic image formed of the cut-out region of interest and/or frame image of interest, and send the dynamic image together with an analysis result image to the image server 3. This can greatly reduce the storage capacity as compared with the case where the dynamic image sent from the imager 1 and an analysis result image obtained by analyzing the dynamic image are stored in the image server 3.

As described above, the controller 21 of the console 2 extracts (i) the region of interest and/or (ii) the frame image of interest from a series of frame images of a dynamic image obtained by dynamic imaging of the chest of a human; sends, of the series of the frame images, only (i) the extracted region of interest, (ii) the extracted frame image of interest or (iii) the extracted region of interest in the extracted frame image of interest to the image server 3; and stores the same in the image DB 31. This can reduce the storage capacity necessary to store a dynamic image and let a doctor see the portion of a dynamic image to be noted in diagnosis efficiently.

For example, the controller 21 identifies, from the series of the frame images of the dynamic image, at least one of a frame image at the maximal expiratory level and a frame image at the maximal inspiratory level; extracts frame images for one respiratory cycle as the frame image of interest based on the identified frame image or frame images; and stores the same in the image DB 31. Thus, only frame images for one respiratory cycle that are important in interpretation about ventilation are stored. This can reduce the storage capacity to store a dynamic image and increase efficiency of re-interpretation of the dynamic image.

Further, for example, the controller 21 detects an abnormal shadow region candidate(s) in each of the frame images of the series (i.e. in each of the frame images of the dynamic image); extracts a frame image(s) in which the abnormal shadow region candidate is detected as the frame image of interest; and stores the same in the image DB 31. Thus, only a frame image(s) in which an abnormality (abnormalities) is present is stored. This can reduce the storage capacity to store a dynamic image and increase efficiency of re-interpretation of the dynamic image.

Further, for example, the controller 21 recognizes the heart region in each of the frame images of the series; extracts frame images for one heartbeat as the frame image of interest based on change in density of the recognized heart region; and stores the same in the image DB 31. Thus, only frame images for one heartbeat that are important in interpretation about perfusion are stored. This can reduce the storage capacity to store a dynamic image and increase efficiency of re-interpretation of the dynamic image.

Further, for example, the controller 21 recognizes a lung field region in, of the series of the frame images of the dynamic image, at least each of the frame image of interest; extracts only a pre-specified part of the recognized lung field region as the region of interest; and stores the same in the image DB 31. Thus, only the specified part in each frame image of a dynamic image or in each frame image of interest among the frame images of the dynamic image is stored. This can reduce the storage capacity to store a dynamic image and increase efficiency of re-interpretation of the dynamic image.

Further, for example, the controller 21 detects an abnormal shadow region candidate(s) in, of the series of the frame images of the dynamic image, at least each of the frame image of interest; extracts only a region containing the detected abnormal shadow region candidate (e.g. a region enclosing the abnormal shadow region candidate or a region enclosing, of the right and left lung fields, a lung field containing the abnormal shadow region candidate) as the region of interest; and stores the same in the image DB 31. Thus, only the region containing an abnormal shadow region candidate in each frame image of a dynamic image or in each frame image of interest among the frame images of the dynamic image is stored. This can reduce the storage capacity to store a dynamic image and increase efficiency of re-interpretation of the dynamic image.

Further, for example, the controller 21 displays the series of the frame images of the dynamic image in the mode in which the region of interest and/or the frame image of interest are recognizable to a user, and changes the region of interest and/or the frame image of interest in response to a user operation(s). This can let a user see whether change of the region of interest and/or the frame image of interest to be stored is necessary, and let him/her change the region of interest and/or the frame image of interest when determining that change thereof is necessary.

The matters described in the above embodiment are merely some preferred examples of the present invention and not intended to limit the present invention.

For example, in the above embodiment, the region of interest and the frame image of interest to be extracted are specified by a user, but may be automatically set. For example, in the case where examination information contains information on the type of diagnosis target (ventilation or perfusion), if the type of diagnosis target is ventilation, frame images for one respiratory cycle may be automatically extracted as the frame image of interest, whereas if the type of diagnosis target is perfusion, frame images for one heartbeat may be automatically extracted as the frame image of interest.

Further, in the above embodiment, the region of interest and the frame image of interest are automatically extracted, but may be extracted in response to user operations.

Further, in the above embodiment, the dynamic image is a dynamic image of a chest, but the subject site is not limited to a chest.

Further, in the above embodiment, the controller 21 that extracts the region of interest and/or the frame image of interest from a series of frame images of a dynamic image and the image DB 31 as a storage are provided in different apparatuses, but may be provided in the same apparatus.

Further, in the above embodiment, when perfusion should be observed carefully (i.e. to be noted), frame images for one heartbeat are extracted and stored as the frame image of interest based on the idea that blood flows over the lung fields by one heartbeat. However, there is another idea that blood reaches the edges of the lung fields by several heartbeats. Hence, based on this idea, the following may be performed: recognize the heart region in each frame image of a dynamic image; identify frame images per heartbeat on the basis of change in density of the recognized heart region; and extract frame images for a predetermined number of heartbeats, the predetermined number being two or more, as the frame image of interest.

Further, in the above, as a computer readable medium for the programs of the present invention, a hard disk, a non-volatile semiconductor memory or the like is used. However, this is not a limit. As the computer readable medium, a portable recording medium, such as a CD-ROM, can also be used. Further, as a medium to provide data of the programs of the present invention, a carrier wave can be used.

In addition to the above, the specific configurations/components and the specific actions of the apparatuses of the dynamic image processing system can also be appropriately modified without departing from the spirit of the present invention.

Although one or more embodiments of the present invention have been described and illustrated in detail, the disclosed embodiments are made for purposes of illustration and example only and not limitation. The scope of the present invention should be interpreted by terms of the appended claims

What is claimed is:

1. A dynamic image processing apparatus comprising:
   a hardware processor that automatically extracts a frame image of interest based on a diaphragm position or an area of a lung field region in each of frame images obtained by dynamic imaging of a subject; and
   an operation unit with which a command to change the automatically extracted frame image of interest is made,
   wherein in response to the command being not made, the hardware processor stores, of the frame images, only the automatically extracted frame image of interest in a storage, and in response to the command being made, the hardware processor stores a post-change frame image of interest in the storage.

2. The dynamic image processing apparatus according to claim 1, wherein the frame images area dynamic image obtained by dynamic imaging of a chest of a human.

3. The dynamic image processing apparatus according to claim 2, wherein the hardware processor:
   identifies, from the frame images, at least one of a frame image at a maximal expiratory level and a frame image at a maximal inspiratory level; and
   extracts frame images including the identified frame image as the frame image of interest.

4. The dynamic image processing apparatus according to claim 2, wherein the hardware processor extracts frame images for at least one respiratory cycle as the frame image of interest.

5. The dynamic image processing apparatus according to claim 3, wherein the hardware processor:
   recognizes the diaphragm position in each of the frame images; and
   identifies the at least one of the frame image at the maximal expiratory level and the frame image at the maximal inspiratory level based on the diaphragm position recognized in each of the frame images.

6. The dynamic image processing apparatus according to claim 3, wherein the hardware processor:
   recognizes the lung field region in each of the frame images; and
   identifies the at least one of the frame image at the maximal expiratory level and the frame image at the maximal inspiratory level based on the area of the lung field region recognized in each of the frame images.

7. The dynamic image processing apparatus according to claim 3, wherein the hardware processor:
   recognizes the lung field region in each of the frame images; and
   identifies the at least one of the frame image at the maximal expiratory level and the frame image at the maximal inspiratory level based on movement of a contour of an outer lateral of the lung field region.

8. The dynamic image processing apparatus according to claim 2, wherein the hardware processor:
   recognizes a heart region in each of the frame images; and
   extracts frame images for a predetermined number of heartbeats, the predetermined number being one or more, as the frame image of interest based on change in density of the recognized heart region.

9. The dynamic image processing apparatus according to claim 2, wherein the hardware processor:
   recognizes the lung field region in, of the frame images, at least each of the frame image of interest; and
   extracts, as a region of interest, only a region enclosing the recognized lung field region or a region enclosing a pre-specified part of the recognized lung field region.

10. The dynamic image processing apparatus according to claim 1, further comprising a display that displays the frame images in a mode in which the frame image of interest is recognizable to a user.

11. A non-transitory computer readable storage medium storing a program to cause a computer to:
   automatically extract a frame image of interest based on a diaphragm position or an area of a lung field region in each of frame images obtained by dynamic imaging of a subject; and
   in response to a command to change the automatically extracted frame image of interest being not made with an operation unit, store, of the frame images, only the automatically extracted frame image of interest in a storage, and in response to the command being made, store a post-change frame image of interest in the storage.

* * * * *